(12) United States Patent
Wright et al.

(10) Patent No.: US 11,395,627 B2
(45) Date of Patent: Jul. 26, 2022

(54) CAUSING A CHANGED BREATHING SEQUENCE BASED ON MEDIA CONTENT

(71) Applicant: Nokia Technologies Oy, Espoo (FI)

(72) Inventors: Christopher Wright, Lausanne (CH); Timothy Beard, Cambridge (GB); David Duffy, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 450 days.

(21) Appl. No.: 16/692,417

(22) Filed: Nov. 22, 2019

(65) Prior Publication Data

US 2020/0178884 A1    Jun. 11, 2020

(30) Foreign Application Priority Data

Dec. 5, 2018    (EP) ..................................... 18210592

(51) Int. Cl.
    *A61B 5/00* (2006.01)
    *G16H 20/30* (2018.01)
    *A61B 5/08* (2006.01)
    *G06N 20/00* (2019.01)

(52) U.S. Cl.
CPC ............ *A61B 5/486* (2013.01); *A61B 5/0816* (2013.01); *A61B 5/7275* (2013.01); *A61B 5/742* (2013.01); *A61B 5/7405* (2013.01); *A61B 5/7455* (2013.01); *G16H 20/30* (2018.01); *G06N 20/00* (2019.01)

(58) Field of Classification Search
CPC ..................................................... A61B 5/486
See application file for complete search history.

(56) References Cited

U.S. PATENT DOCUMENTS

| | | | |
|---|---|---|---|
| 5,076,281 A | 12/1991 | Gavish | |
| 7,255,672 B2 | 8/2007 | Elliott | |
| 9,330,680 B2 | 5/2016 | Kassam et al. | |
| 11,089,994 B2 * | 8/2021 | Goldstein | A61B 5/7264 |

(Continued)

FOREIGN PATENT DOCUMENTS

| | | |
|---|---|---|
| CN | 106108905 A | 11/2016 |
| EP | 1587060 A1 | 10/2005 |

(Continued)

OTHER PUBLICATIONS

International Search Report and Written Opinion received for corresponding Patent Cooperation Treaty Application No. PCT/EP2019/082655, dated Jan. 15, 2020, 11 pages.

(Continued)

*Primary Examiner* — Travis R Hunnings
(74) *Attorney, Agent, or Firm* — Nokia Technologies Oy

(57) ABSTRACT

An apparatus comprising means for: obtaining a predicted breathing sequence of a user; obtaining a first time when it is predicted that a first media content will be rendered to the user; obtaining a desired breathing phase for consuming the first media content; and causing at least one stimulus to be provided to the user, the at least one stimulus configured to cause a changed breathing sequence instead of the predicted breathing sequence, wherein the desired breathing phase in the changed breathing sequence is temporally shifted towards the first time as compared to the desired breathing phase in the predicted breathing sequence.

20 Claims, 9 Drawing Sheets

(56) References Cited

U.S. PATENT DOCUMENTS

| | | | |
|---|---|---|---|
| 2006/0224046 | A1 | 10/2006 | Ramadas et al. |
| 2007/0173684 | A1 | 7/2007 | Elliott |
| 2008/0319333 | A1 | 12/2008 | Gavish et al. |
| 2011/0183305 | A1 | 7/2011 | Orbach |
| 2016/0055420 | A1 | 2/2016 | Karanam et al. |
| 2016/0314698 | A1* | 10/2016 | Saada .................... G09B 19/00 |
| 2017/0068994 | A1 | 3/2017 | Slomkowski et al. |
| 2017/0249855 | A1 | 8/2017 | Gazzaley |
| 2017/0354795 | A1 | 12/2017 | Blahnik et al. |
| 2017/0367651 | A1 | 12/2017 | Tzvieli et al. |
| 2020/0383647 | A1* | 12/2020 | Freeman ............ A61B 5/02055 |

FOREIGN PATENT DOCUMENTS

| | | |
|---|---|---|
| EP | 2805674 A1 | 11/2014 |
| WO | 2015/087318 A1 | 6/2015 |
| WO | 2016/074042 A1 | 5/2016 |
| WO | 2018/160749 A1 | 9/2018 |

OTHER PUBLICATIONS

Office action received for corresponding European Patent Application No. 18210591.6, dated Aug. 12, 2021, 5 pages.

"Newfound Neurological Mechanism Explains how Breathing can Sharpen Your Focus", New Atlas, Retrieved on Nov. 19, 2019, Webpage available at: https://newatlas.com/breathing-brain-attention-focus-meditation/54601/.

"Neuroscience Research Shows the Brain is Strobing, not Constant", The University of Sydney, Retrieved on Nov. 19, 2019, Webpage available at: https://sydney.edu.au/news-opinion/news/2017/11/17/neuroscience-research-shows-the-brain-is-strobing-not-constant-.html.

"Rhythm of Breathing Affects Memory and Fear", Neuroscience, Retrieved on Nov. 19, 2019, Webpage available at: https://neurosciencestuff.tumblr.com/post/159167946726/rhythm-of-breathing-affects-memory-and-fear#_=_.

"The Yogi Masters were Right—Meditation and Breathing Exercises Can Sharpen Your Mind", Science Daily, Retrieved on Nov. 19, 2019, Webpage available at : https://www.sciencedaily.com/releases/2018/05/180510101254.htm.

Sato et al., "A Playback System that Synchronizes the Musical Phrases with Listener's Respiration Phases", Extended Abstracts on Human Factors in Computing Systems, Apr. 27-May 2, 2013, pp. 1035-1040.

"Self-Care Apps are Booming", TechCrunch, Retrieved on Nov. 19, 2019, Webpage available at : https://techcrunch.com/2018/04/02/self-care-apps-are-booming/.

"What is the Science Behind the Apple Watch "Breathe" App in watchOS 3?", MacTrast, Retrieved on Nov. 19, 2019, Webpage available at : https://www.mactrast.com/2016/09/science-behind-apple-watch-breathe-app-watchos-3/.

Sato et al., "Increase in the Timing Coincidence of a Respiration Event Induced by Listening Repeatedly to the Same Music Track", Acoustical Science and Technology, vol. 33, No. 4, 2012, pp. 255-261.

Sato et al., "Audience Excitement Reflected in Respiratory Phase Synchronization", IEEE International Conference an Systems, Man, and Cybernetics (SMC), Oct. 5-8, 2017, pp. 2856-2860.

Capellan et al., "Changes in Breathing while Listening to Read Speech: The Effect of Reader and Speech Mode", Frontiers in Psychology, 2013, pp. 1-29.

"Suspense Really is in the Air in a Good Movie: Films have Their Own 'Signature' in the Breath of Viewers—and Researchers can Even Use it to Tell What Scene They're Watching", Daily Mail Online, Retrieved on Nov. 20, 2019, Webpage available at : https://www.dailymail.co.uk/sciencetech/article-3587636/Suspense-really-air-good-movie-Researcher-say-film-signature-breath-viewers.html.

"How AI-Generated Music is Changing the Way Hits are Made", The Verge, Retrieved on Nov. 20, 2019, Webpage available at : https://www.theverge.com/2018/8/31/17777008/artificial-intelligence-taryn-southern-amper-music.

"What News-Writing Bots Mean for the Future of Journalism", Wired, Retrieved on Nov. 20, 2019, Webpage available at : https://www.wired.com/2017/02/robots-wrote-this-story/.

"IBM Watson Creates the First AI-Made Film Trailer—and it's Incredibly Creepy", Wired, Retrieved on Nov. 20, 2019, Webpage available at : https://www.wired.co.uk/article/IBM-watson-ai-film-trailer.

"AI Can Write Surprisingly Scary and Creative Horror Stories", Engadge, Retrieved on Nov. 20, 2019, Webpage available at : https://www.engadget.com/2017/10/31/shelley-ai-writes-horror-stories-on-twitter/.

"You Asked: Is It Bad for You to Read the News Constantly?", TIME, Retrieved on Nov. 20, 2019, Webpage available at : https://time.com/5125894/is-reading-news-bad-for-you/.

"Body Driven Music", Rockmyrun, Retrieved on Nov. 22, 2019, Webpage available at : http://www.rockmyrun.com/myBeat.php.

Ghandeharioun et al., "BrightBeat: Effortlessly Influencing Breathing for Cultivating Calmness and Focus", Proceedings of the 2017 CHI Conference Extended Abstracts on Human Factors in Computing Systems, May 6-11, 2011, pp. 1624-1631.

Prpa et al., "Attending to Breath: Exploring How the Cues in a Virtual Environment Guide the Attention to Breath and Shape the Quality of Experience to Support Mindfulness", Proceedings of the 2018 Designing Interactive Systems Conference, Jun. 9-13, 2018, pp. 71-84.

"Use the Breathe app", Apple Support, Retrieved on Nov. 22, 2019, Webpage available at : https://support.apple.com/en-gb/HT206999.

"Biohack Your Breathing", Breathesync, Retrieved on Nov. 22, 2019, Webpage available at : https://www.breathesync.com/.

Extended European Search Report received for corresponding European Patent Application No. 18210591.6, dated Feb. 21, 2019, 7 pages.

Extended European Search Report received for corresponding European Patent Application No. 18210592.4, dated May 14, 2019, 7 pages.

Office action received for corresponding European Patent Application No. 18210591.6, dated Mar. 9, 2022, 5 pages.

Office action received for corresponding European Patent Application No. 18210592.4, dated Apr. 7, 2022, 4 pages.

* cited by examiner

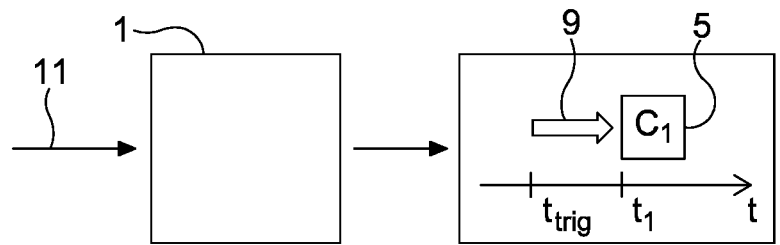
FIG. 3
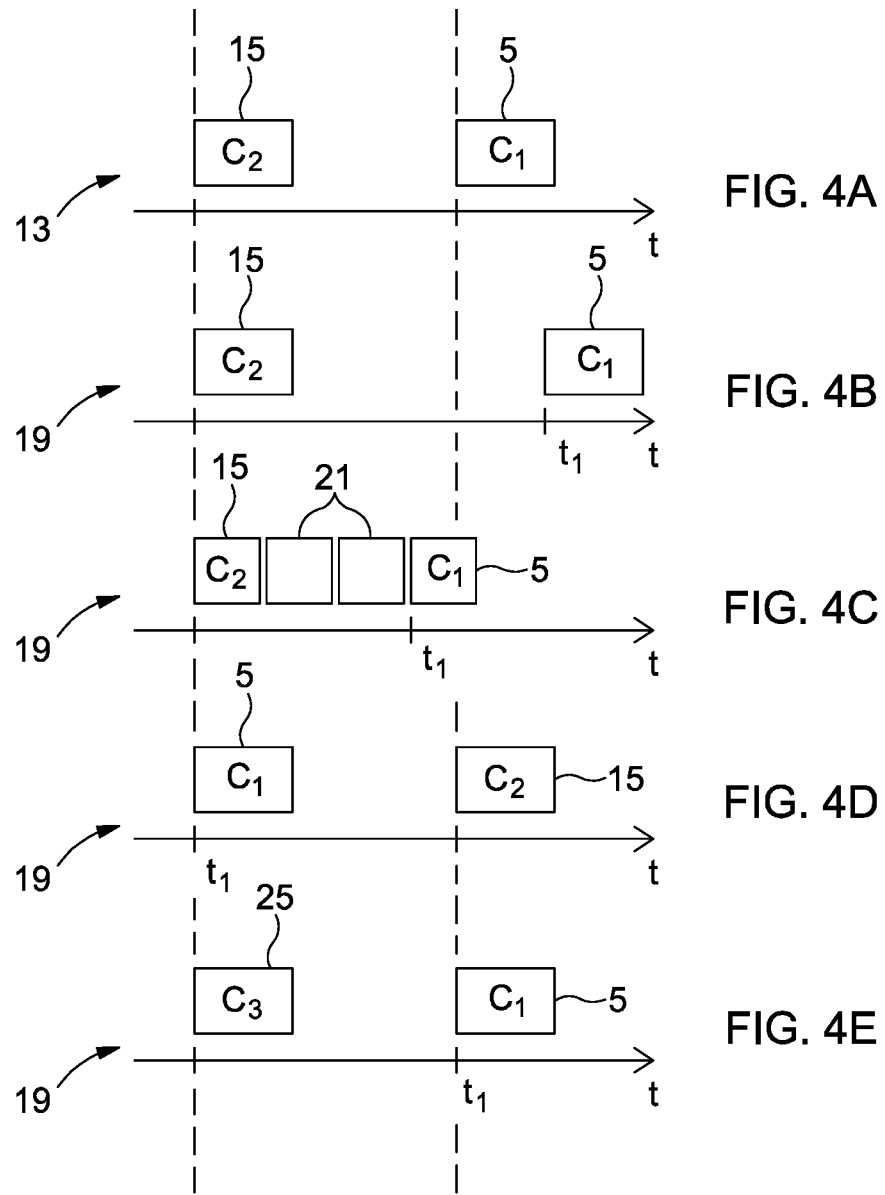
FIG. 4A
FIG. 4B
FIG. 4C
FIG. 4D
FIG. 4E

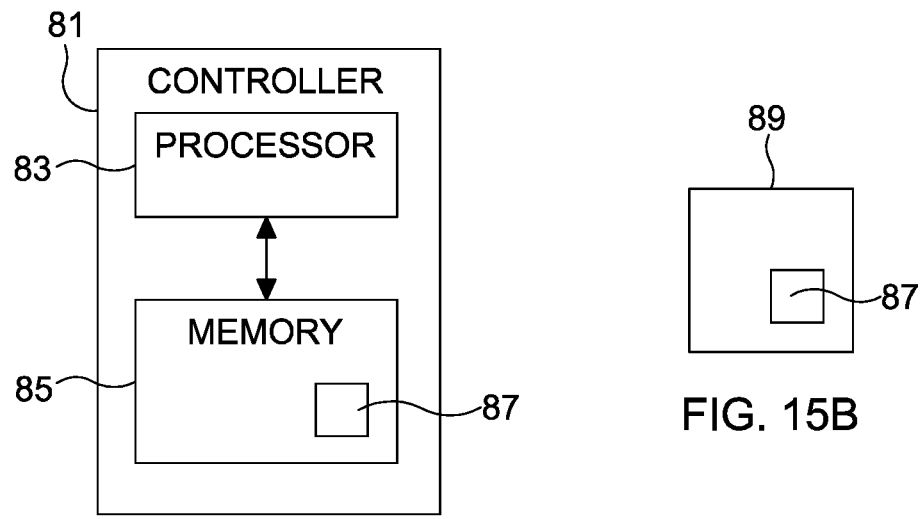
FIG. 15A
FIG. 15B
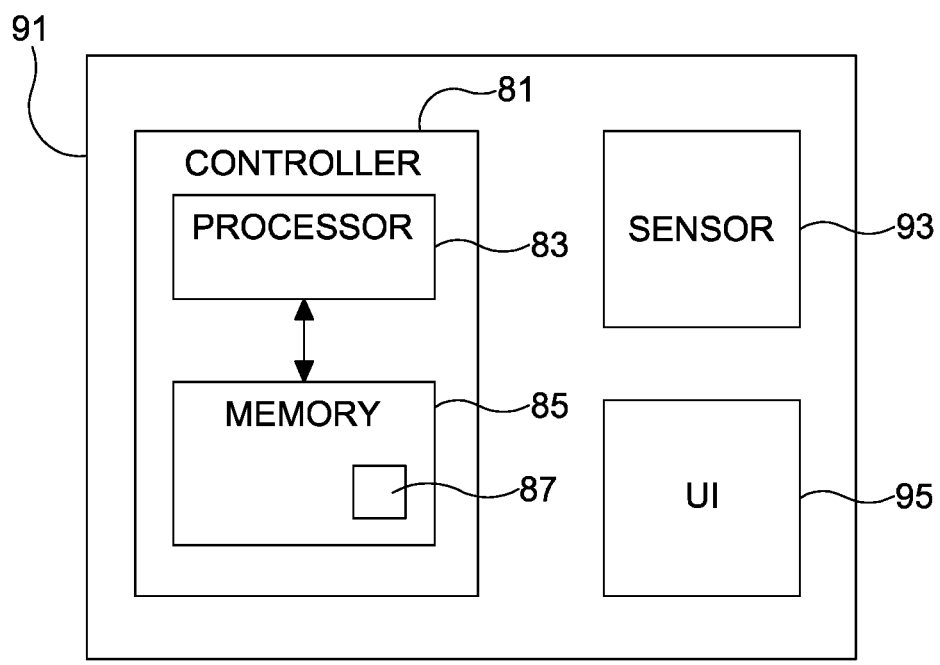
FIG. 16

CAUSING A CHANGED BREATHING SEQUENCE BASED ON MEDIA CONTENT

TECHNOLOGICAL FIELD

Example embodiments of the present disclosure relate to causing a changed breathing sequence based on media content. Some example embodiments relate to apparatus, methods, and computer programs for causing a changed breathing sequence based on media content.

BACKGROUND

Brain functions such as, for example, attention, response to stimuli, and memory are known to follow rhythmic oscillations in different frequency bands. It has been found that these oscillations can be entrained through breathing. Therefore, attention, response to stimuli, and memory in respect of an input varies in dependence upon whether the input is received while inhaling or while exhaling.

BRIEF SUMMARY

According to various, but not necessarily all, embodiments there is provided an apparatus comprising means for: obtaining a predicted breathing sequence of a user; obtaining a first time when it is predicted that a first media content will be rendered to the user; obtaining a desired breathing phase for consuming the first media content; and causing at least one stimulus to be provided to the user, the at least one stimulus configured to cause a changed breathing sequence instead of the predicted breathing sequence, wherein the desired breathing phase in the changed breathing sequence is temporally shifted towards the first time as compared to the desired breathing phase in the predicted breathing sequence.

According to various, but not necessarily all, embodiments there is provided an apparatus comprising: at least one processor; and at least one memory including computer program code, the at least one memory and the computer program code configured to, with the at least one processor, cause the apparatus at least to perform: obtaining a predicted breathing sequence of a user; obtaining a first time when it is predicted that a first media content will be rendered to the user; obtaining a desired breathing phase for consuming the first media content; and causing at least one stimulus to be provided to the user, the at least one stimulus configured to cause a changed breathing sequence instead of the predicted breathing sequence, wherein the desired breathing phase in the changed breathing sequence is temporally shifted towards the first time as compared to the desired breathing phase in the predicted breathing sequence.

According to various, but not necessarily all, embodiments there is provided an electronic device comprising: the apparatus of either of the preceding paragraphs; at least one breathing sensor configured to enable the predicted breathing sequence of the user to be obtained; and at least one user interface configured to provide the at least one stimulus to the user.

According to various, but not necessarily all, embodiments there is provided a method comprising: obtaining a predicted breathing sequence of a user; obtaining a first time when it is predicted that a first media content will be rendered to the user; obtaining a desired breathing phase for consuming the first media content; and causing at least one stimulus to be provided to the user, the at least one stimulus configured to cause a changed breathing sequence instead of the predicted breathing sequence, wherein the desired breathing phase in the changed breathing sequence is temporally shifted towards the first time as compared to the desired breathing phase in the predicted breathing sequence.

In some examples the method comprises obtaining at least the first media content and obtaining metadata which tags specific media content so that the specific media content is associated with a particular desired breathing phase.

According to various, but not necessarily all, embodiments there is provided a computer program that, when run on a computer, performs: obtaining a predicted breathing sequence of a user; obtaining a first time when it is predicted that a first media content will be rendered to the user; obtaining a desired breathing phase for consuming the first media content; and causing at least one stimulus to be provided to the user, the at least one stimulus configured to cause a changed breathing sequence instead of the predicted breathing sequence, wherein the desired breathing phase in the changed breathing sequence is temporally shifted towards the first time as compared to the desired breathing phase in the predicted breathing sequence.

According to various, but not necessarily all, embodiments there is provided a non-transitory computer readable medium comprising program instructions stored thereon for performing at least the following: obtaining a predicted breathing sequence of a user; obtaining a first time when it is predicted that a first media content will be rendered to the user; obtaining a desired breathing phase for consuming the first media content; and causing at least one stimulus to be provided to the user, the at least one stimulus configured to cause a changed breathing sequence instead of the predicted breathing sequence, wherein the desired breathing phase in the changed breathing sequence is temporally shifted towards the first time as compared to the desired breathing phase in the predicted breathing sequence.

According to various, but not necessarily all, embodiments there is provided examples as claimed in the appended claims.

The following portion of this 'Brief Summary' section, describes various features that may be features of any of the embodiments described in the foregoing portion of the 'Brief Summary' section. The description of a function should additionally be considered to also disclose any means suitable for performing that function.

The at least one stimulus may comprise at least one of an audio, visual, haptic output to the user.

The at least one stimulus may have a tempo configured to entrain a breathing sequence of the user to cause the changed breathing sequence.

Causing the at least one stimulus to be provided to the user may comprise rendering a second media content to the user prior to the first media content, the second media content being determined to at least partially cause the changed breathing sequence.

The second media content may be rendered to the user instead of a third media content, wherein the third media content precedes the first media content in an original timeline.

In some examples, a desired breathing phase for consuming another media content comprised in a sequence comprising the first media content is obtained; a difference measure between the first media content and the another media content with respect to the corresponding desired breathing phases is determined; and the changed breathing sequence to minimize the difference measure is determined.

The predicted breathing sequence may be based, at least in part, on a measured breathing rate of the user and a measured breathing phase of the user.

The predicted breathing sequence may be based, at least in part, on a user profile, wherein the user profile is used to predict divergence of breathing phases of the user from breathing phases of different users over time based on media content.

Obtaining the desired breathing phase for consuming a first media content may comprise reading metadata associated with the first media content.

BRIEF DESCRIPTION

Some example embodiments will now be described with reference to the accompanying drawings in which:

FIG. 3 shows an example of a delayed rendering as described herein;

FIG. 4A shows an example of an original timeline as described herein;

FIG. 4B shows an example of a sequence of rendering as described herein;

FIG. 4C shows another example of a sequence of rendering as described herein;

FIG. 4D shows another example of a sequence of rendering as described herein;

FIG. 4E shows another example of a sequence of rendering as described herein;

FIG. 15A shows an example of a controller as described herein;

FIG. 15B shows an example of a delivery mechanism as described herein;

FIG. 16 shows an example of a device as described herein; and

DETAILED DESCRIPTION

Figure 1:
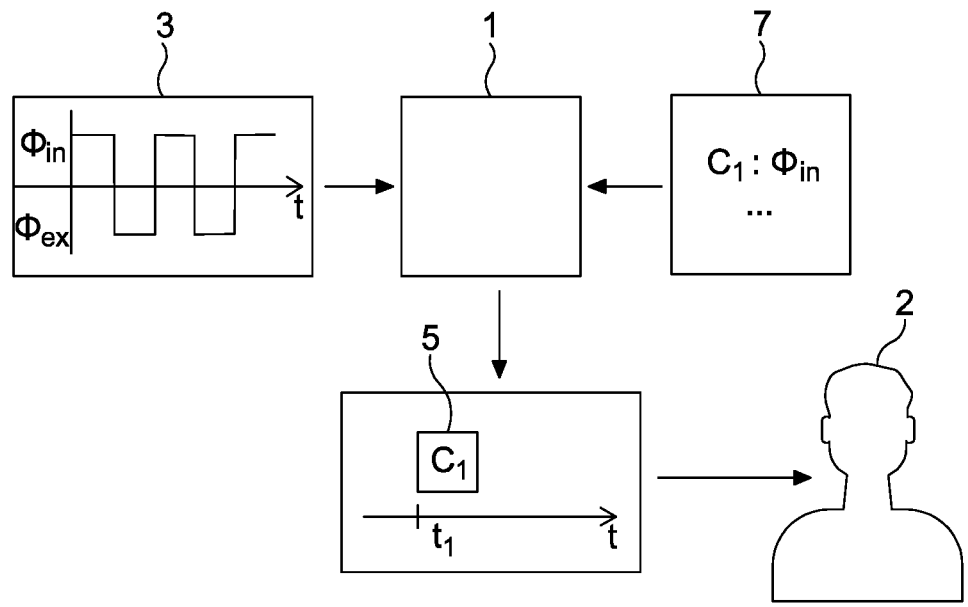
FIG. 1 shows an example of an apparatus as described herein.

FIG. 1 schematically illustrates an example of an apparatus 1 for, from the perspective of a user 2, causing improved temporal alignment of a first media content 5 with a desired breathing phase 7 for consuming the first media content 5.

The first media content 5 may take the form of video, audio, graphics, text, images, icons or the like and may include multimedia content. The first media content 5 may be comprised in a file at the apparatus 1 or some other discrete unit. Alternatively, the first media content 5 may be comprised in a continuous stream such as a news feed or a live stream. In some examples the first media content 5 may be a portion or extract of the video, audio, text, or other media format. For example, the first media content 5 may be a sentence in a longer piece of text or may be a frame or scene from a video. Consuming the media content comprises, for example, watching video, listening to audio, or reading text, etc.

Breathing (respiration) comprises two major phases. One breathing phase is inhalation (inspiration), referenced as $\Phi_{in}$ in the FIGS. Inhalation involves the contraction of a diaphragm and intercostal muscles to cause expansion of the chest cavity and thus air to flow into the lungs. Another breathing phase is exhalation (expiration), referenced as $\Phi_{ex}$ in the FIGS. Exhalation involves the relaxation of the diaphragm and intercostal muscles to cause a reduction in the volume of the chest cavity and thus air to flow out of the lungs.

The apparatus 1 obtains a predicted breathing sequence 3 of a user 2. The predicted breathing sequence 3 indexes breathing phases (inhalation and exhalation) to time. The predicted breathing sequence 3 therefore enables a breathing phase at a given future point in time to be predicted.

In some examples the apparatus 1 receives data in order to obtain the predicted breathing sequence 3 of the user 2, or processes received data to obtain the predicted breathing sequence 3 of the user 2, or obtains the predicted breathing sequence 3 of the user 2 by calculation.

The apparatus 1 obtains the desired breathing phase 7 for consuming the first media content 5. Since brain activity is found to vary with different breathing phases and different levels of brain activity can be advantageous for consuming different media content, the desired breathing phase 7 is one which correlates with a level of brain activity which is judged to be advantageous for consuming the particular first media content 5.

For example, where the first media content 5 comprises information which is considered to be of significant importance for the user 2 to comprehend, it is advantageous to provide this information to the user 2 while the user 2 experiences a state of heightened attention (increased brain activity). The desired breathing phase 7 for causing a state of heightened attention has been found to be inhalation.

Where the first media content 5 comprises information which is considered to be stressful for the user 2, it can be advantageous to provide this information to the user 2 while the user 2 experiences a state in which their stress response is reduced (reduced brain activity) in order to improve the emotional wellbeing of the user 2. The desired breathing phase 7 for causing a state of heightened attention has been found to be exhalation.

In some examples the desired breathing phase 7 is a breathing phase which correlates with a level of brain activity which is judged to be advantageous for consuming the particular first media content 5 and additionally has a duration similar to that predicted for the user 2 to consume the first media content 5. In some examples, the duration of such a breathing phase matches or exceeds that predicted for the user 2 to consume the first media content 5 so that the first media content 5 can be consumed by the user 2 in full whilst the user 2 experiences the desired state for consuming it.

In some examples the breathing phases are subdivided. The breathing phases comprise a number of subdivisions of inhalation and a number of subdivisions of exhalation. The desired breathing phase 7 may refer to one of these subdivisions.

In examples where the apparatus 1 causes other media content to be rendered to the user 2 in addition to the first media content 5, the apparatus 1 also obtains corresponding desired breathing phases for consuming the other media content.

In some examples the apparatus 1 receives data in order to obtain the desired breathing phase 7, or processes received data to obtain the desired breathing phase 7, or obtains the desired breathing phase 7 by calculation.

In some examples the desired breathing phase 7 for consuming the media content 5 is obtained by reading metadata associated with the first media content 5. The apparatus 1 may obtain this metadata. The metadata tags specific media content so that the specific media content is associated with a particular desired breathing phase. The metadata may comprise data about a desired breathing phase or may comprise data which can be correlated with a desired breathing phase. Such data that can be correlated with a desired breathing phase may include indicators of emotional tone, meaning, comprehension importance, etc. of the media content. The data that can be correlated with desired breathing phase may also include indicators of the goals of the media content such as, for example, education, entertainment, relaxation, etc.

In other examples the desired breathing phase 7 for consuming the media content 5 is obtained by analysis and classification of features of the first media content 5. The analysis and classification of features of the first media content 5 may be performed by the apparatus 1. For example, emotional tone, meaning, comprehension importance of the first media content 5, and/or goals of the first media content 5 such as education, relaxation, etc., which may be correlated with a desired breathing phase, can be determined by analyzing, for example, densities of key words in text or, for example, analysis of characteristic audio profiles in video or audio. By way of an example, a jump scare in a video may be determined based on detection of an audio profile indicative of sudden noise.

The apparatus 1 causes rendering of the first media content 5 to the user 2 at a first time $t_1$. The first time $t_1$ is based, at least in part, on a predicted time in the predicted breathing sequence 3 at which the desired breathing phase 7 occurs.

Rendering the first media content 5 puts the first media content 5 into a format in which it can be perceived by the user 2. The first media content 5 may be rendered to the user 2 as a visual output from a display, as an audio output from a speaker, or as another perceptible output from another user interface.

Figure 2:
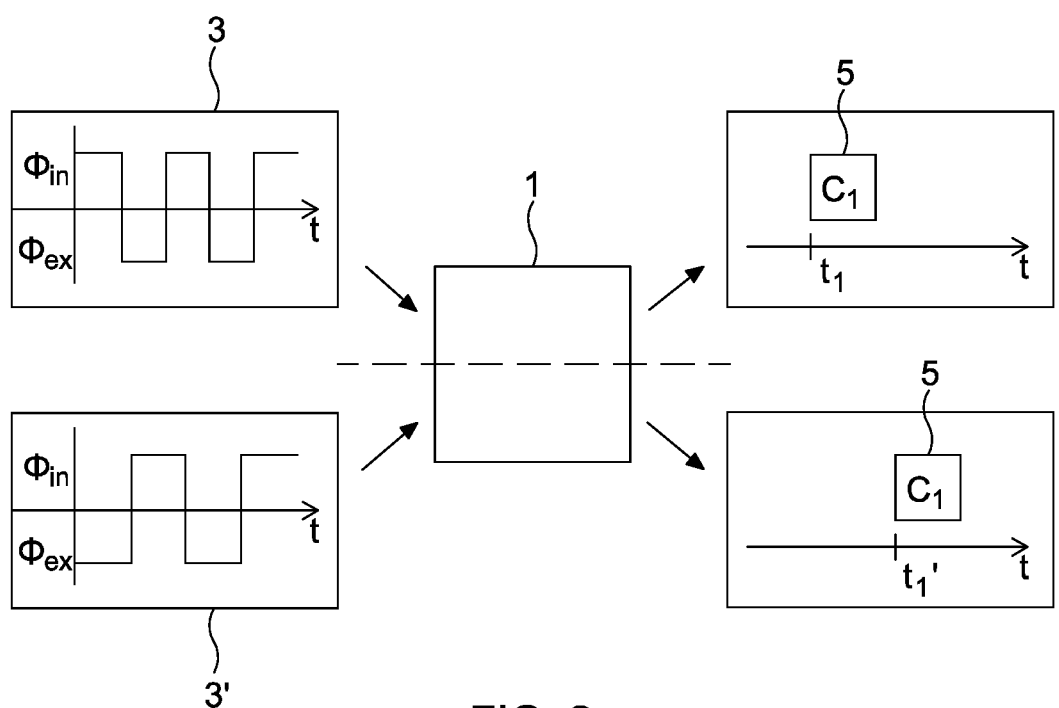
FIG. 2 shows an example of different rendering times as described herein.

Since the first time $t_1$ is determined based on a temporal relationship between the obtained desired breathing phase 7 and the obtained predicted breathing sequence 3, the apparatus 1 causes rendering of the same first media content 5 to the same user 2 at different first times $t_1$, $t_1'$ for different obtained predicted breathing sequences 3, 3' as schematically illustrated in FIG. 2.

Returning to FIG. 1, it can be seen in this example that rendering the first media content 5 at the first time $t_1$ results in temporal alignment of the first media content 5 and the desired breathing phase 7. In other examples, however, rendering the first media content 5 at the first time $t_1$ may not result in the first media content 5 exactly coinciding with the desired breathing phase 7. The first time $t_1$ may be determined by minimization of a difference measure in relation to a plurality of media content as described in relation to FIG. 5 below.

FIG. 3 schematically illustrates an example of how the apparatus 1 can control the time of rendering of the first media content 5 to the user 2. In this example, the apparatus 1 controls the delay 9 between an input 11 to trigger rendering of the first media content 5 and rendering of the first media content 5 at the first time $t_1$.

In some examples the input 11 to trigger rendering of the first media content 5 comprises receipt, for immediate rendering, of the first media content 5 at the apparatus 1. For example, the first media content 5 may be a notification such as, for example, a news alert. The apparatus 1 receives the notification and obtains a breathing phase 7 during which it is desirable for the user 2 to receive that notification. So that the rendering of the notification to the user 2 is synchronized with the desired breathing phase 7, the apparatus 1 can control the delay 9 between receipt of the notification at the apparatus 1 and the rendering of the notification to the user at the first time $t_1$. This may be similarly applicable to, for example, the receipt of media content comprised in a live stream.

In some examples, the input 11 to trigger rendering of the first media content 5 comprises the generation, for immediate rendering, of the first media content 5 at the apparatus 1. For example, the first media content 5 may be AI-generated media content, generated at the apparatus 1. The AI-generated media content is not be rendered immediately upon generation but is instead rendered after a delay 9 which is controlled by the apparatus 1 in order to temporally align the rendering of the AI-generated media content with the desired breathing phase 7 for consuming said AI-generated media content.

FIGS. 4A to 4E schematically illustrate examples of how the rendering of media content which is associated with an original timeline 13 can be controlled to improve temporal alignment with corresponding desired breathing phases.

FIG. 4A schematically illustrates an example of an original time line 13 which defines an originally specified temporal relationship between the first media content 5 and a second media content 15. The original timeline 13 or the originally specified temporal relationships between different media content may be recorded in metadata associated with the first and second media content 5, 15.

The original timeline 13 defines an order for the first and second media content 5, 15 and any preceding, intervening, or subsequent media content that is also associated with the original timeline 13. In the illustrated example the second media content 15 precedes the first media content 5 in the original timeline 13. In some examples, such as those illustrated in FIGS. 4B and 4C, the sequence of rendering 19 follows this order. However, the temporal relationships, at rendering, between the first media content 5 and the second media content 15 may differ from the original timeline 13.

In some examples, the apparatus 1 causes rendering of the first media content 5 to the user 2 at the first time $t_1$ by controlling a temporal relationship between the first media content 5 and the second media content 15, which precedes the first media content 5 in a sequence of rendering 19.

The temporal relationship, at rendering, between the first media content 5 and the second media content 15 may be based on the original timeline 13 and a predicted rate of consumption of the media content by the user 2.

The predicted rate of consumption of the media content by the user 2 may be based on current or historic data regarding the user 2 such as, for example, the reading speed of the user 2 or the scrolling speed of the user 2. In some examples the predicted rate of consumption of the media content by the user 2 is also based on the media content. For example, the predicted rate of consumption of the media content by the user 2 can be based upon the rate at which the user 2 has, historically, consumed similar media content. Similar media content have a common classification, a common source, or one or more common key features. In other examples the predicted rate of consumption of the media content by the user 2 can be based upon the rate at which one or more other users have consumed the media content. The predicted rate of consumption of the media content by the user 2 may also vary based on the environment and/or mood in which the user 2 will receive the media content.

The originally specified temporal relationships defined in the original timeline 13 may be based on a length of the media content and/or any intervening media content. For example, the originally specified temporal relationships may be based on a number of video frames between the first and second media content 5, 15, a number or words between the first and second media content 5, 15, or a duration of the interval, played at a normal speed with no pausing, between the first and second media content 5, 15.

FIG. 4B schematically illustrates an example in which the control of the temporal relationship, at rendering, between the first media content 5 and the second media content 15, which precedes the first media content 5 in a sequence of rendering 19, comprises introducing a delay between the second media content 15 and the first media content 5.

The apparatus 1 can control this delay by adjusting a response time. Examples of controllable response times comprise a time taken to respond to a user input or a time to respond to a control signal to render one or more media content comprised in the sequence 19. The apparatus 1 controls the delay between the second media content 15 and the first media content 5 in order to improve temporal alignment between the rendering of the first media content 5 and the desired breathing phase 7 for consuming the first media content 5.

FIG. 4C schematically illustrates another example of controlling a temporal relationship between the first media content 5 and the second media content 15. In this example, a rate of rendering is changed in order to improve temporal alignment between the rendering of the first media content 5 and the desired breathing phase 7 for consuming the first media content 5.

The apparatus 1 changes a rate at which one or more of: the second media content 15; the first media content 5; and other, intervening media content 21 in the sequence 19 between the second media content 15 and the first media content 5 is rendered to the user 2.

In some examples the rate of rendering media content in the sequence of rendering 19 to the user 2 may be synchronized with rhythms in the predicted breathing sequence 3 of the user 2.

FIG. 4D schematically illustrates another example of controlling a temporal relationship between the first media content 5 and the second media content 15. In this example, controlling the temporal relationship between the first media content 5 and the second media content 15 comprises switching the order of the first media content 5 and the second media content 15 in the sequence of rendering 19, as compared to the original timeline 13. For example, in a multimedia presentation the order in which an image and a text extract may be presented is switched so that one or other of the image and text extract is temporally aligned with the corresponding desired breathing phase for consuming that image or text extract.

FIG. 4E schematically illustrates an example of rendering which differs from an original timeline 13. In this example, a third media content 25 is rendered to the user 2 instead of the second media content 15. The third media content 25 is predicted to have a different effect on the breathing sequence of the user 2 in comparison to the second media content 15. The third media content 25 is selected because this difference in effect is predicted to shift the timing of the desired breathing phase 7 for consuming the first media content 5 so that it more closely coincides with the time $t_1$ of rendering of the first media content 5.

Additionally or alternatively, the third media content 25 may be of a different duration than the second media content 15, thus increasing or decreasing the time taken to render the media content which precedes the first media content 5 in the sequence of rendering 19. As a result, the time $t_1$ at which the first media content 5 will be rendered to a user is temporally shifted.

Figure 5:
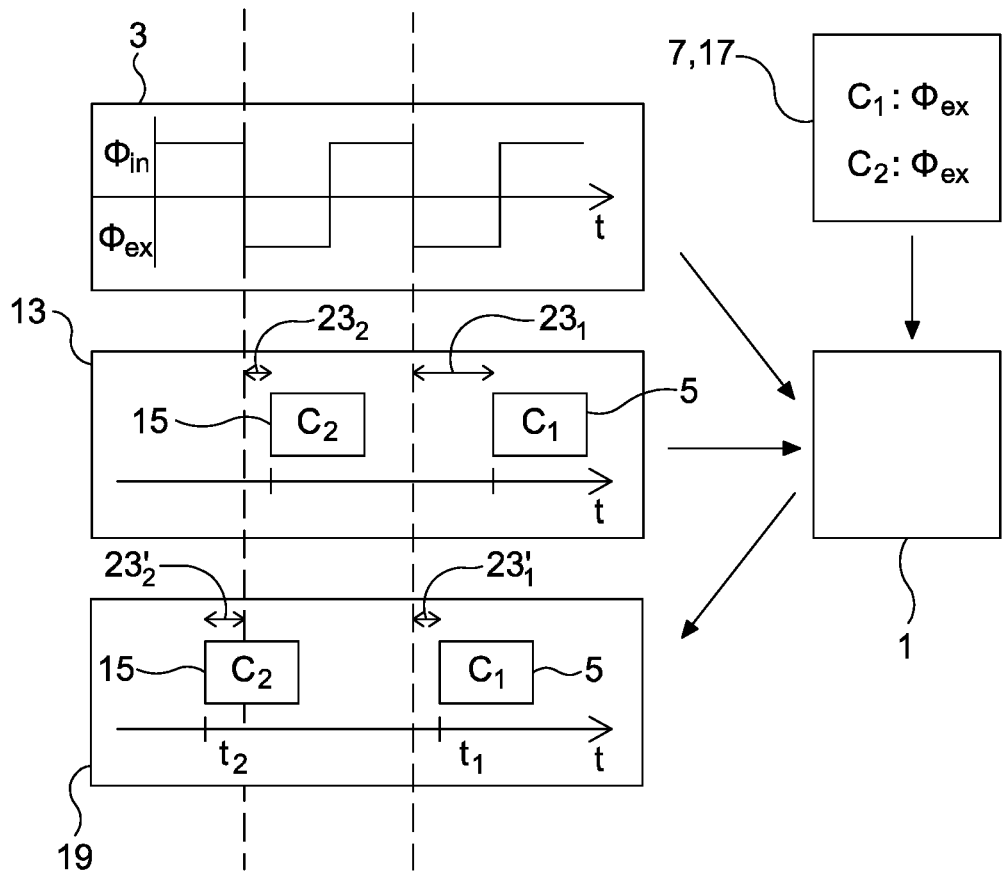
FIG. 5 shows an example of controlling temporal relationships in a sequence of rendering as described herein.

FIG. 5 schematically illustrates an example of how the apparatus 1 can cause a schedule of rendering 19 which minimizes a difference measure between media content, such as the first media content 5 and the second media content 15, and corresponding desired breathing phases, such as desired breathing phase 7 for consuming the first media content 5 and desired breathing phase 17 consuming the second media content 15.

In this example, the apparatus 1 obtains the desired breathing phase 7 for consuming the first media content 5 and the desired breathing phase 17 for consuming the second media content 15.

The apparatus 1 compares a predicted time in the predicted breathing sequence 3 at which the desired breathing phase 7 occurs with timing of the first media content 5 in the original timeline 13 to obtain a difference $23_1$. Likewise, the apparatus 1 compares a predicted time in the predicted breathing sequence 3 at which the desired breathing phase 17 occurs with timing of the second media content 15 in the original timeline 13 to obtain a difference $23_2$.

These differences $23_1$, $23_2$ between the timings of the first and second media content 5, 15 in the original timeline 13 and the predicted times of the desired breathing phases 7, 17 in the predicted breathing sequence 3 are used to determine a difference measure.

The apparatus 1 controls the temporal relationship between the first media content 5 and the second media content 15 in order to minimize the difference measure.

In the resulting sequence of rendering 19, the first media content 5 is rendered to the user 2 at the first time $t_1$ which differs from a predicted time in the predicted breathing sequence 3 at which the desired breathing phase 7 occurs by a difference $23_1'$. The difference $23_1'$, at rendering, may differ from the difference $23_1$ between the timing of the first media content 5 in the original timeline 13 and the predicted time at which the desired breathing phase 7 occurs in the predicted breathing sequence 3.

In the resulting sequence of rendering 19, the second media content 15 is rendered to the user 2 at a second time $t_2$ which differs from a predicted time in the predicted breathing sequence 3 at which the desired breathing phase 17 occurs by a difference $23_2'$. The difference $23_2'$, at rendering, may differ from the difference $23_2$ between the timing of the second media content 15 in the original timeline 13 and the predicted time at which the desired breathing phase 17 occurs in the predicted breathing sequence 3.

Individually the differences $23_1'$ and $23_2'$ may not each be reduced as compared to the differences $23_1$ and $23_2$. For example, in the example of FIG. 5 it can be seen that the difference $23_2'$ has increased slightly as compared to the difference $23_2$, however the difference $23_1'$ has reduced significantly as compared to the difference $23_1$ such that the overall temporal deviation of the rendering of the first and second media content 5, 15 from corresponding desired breathing phases 7, 17 is reduced.

The difference measure may be a cost function. The difference measure may be minimized in the presence of constraints. The constraints may be soft constraints or hard constraints or a mixture of both.

Soft constraints may include the extent to which temporally shifting the time of rendering of media content is noticeable to the user 2. The extent of the temporal shift of shifting the time of rendering of media content may be penalized in the difference measure commensurate with the extent to which the temporal shift is noticeable.

Different examples of how the rendering of media content can be controlled to improve temporal alignment with corresponding desired breathing phases, such as those of FIGS. 4B to 4E, are differently noticeable to users and may therefore carry different penalties in the difference measure. The penalties can be pre-defined or can be affected by one or more of, for example, the user, their current mood and environment, or the type of media content at issue.

Soft constraints may also include different weightings in respect of different media content such that differences between time of rendering and a time when a corresponding desired breathing phase is predicted to occur in respect of certain media content are more heavily penalized than in respect of other media content in the difference measure.

Hard constraints may include a requirement that a certain one or more media content is rendered at the time when a corresponding desired breathing phase is predicted to occur.

The different weightings in respect of different media content are based on an importance of temporally aligning the rendered media content with the corresponding desired breathing phase in view of achieving the overall goal of rendering the media content associated with the original timeline 13. The certain media content for which there is a requirement for temporal alignment between the time of rendering and the corresponding desired breathing phase may have an importance to achieving the overall goal of rendering the media content associated with the original timeline 13 which exceeds a threshold condition.

Alternatively, the different weightings in respect of different media content may be based on pre-existing metrics of importance of likely interest to the user 2, such as number of likes on a social media feed. Likewise, the certain media content for which there is a requirement for temporal alignment between the time of rendering and the corresponding desired breathing phase may be those which, in view of such pre-existing metrics, are judged to have an importance which exceeds a threshold condition.

Figure 6:
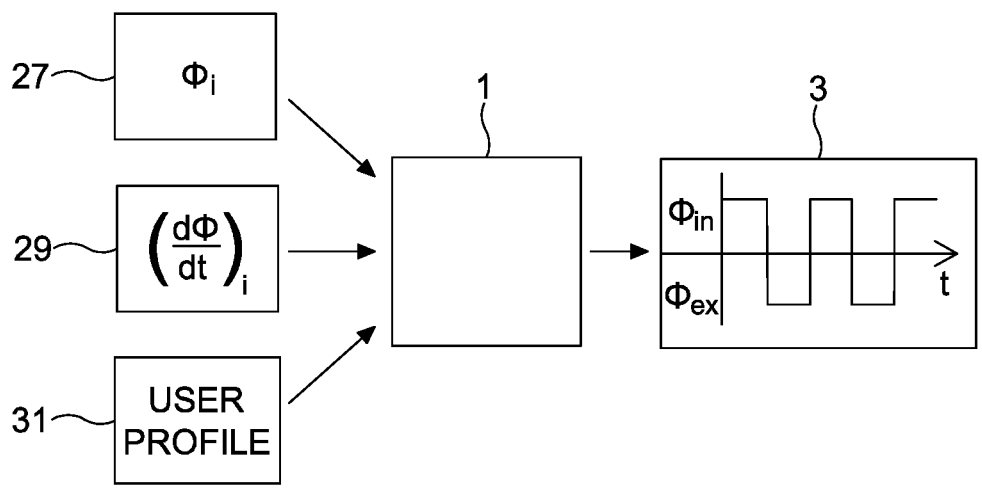
FIG. 6 shows an example of predicting a breathing sequence of a user as described herein.

FIG. 6 schematically illustrates an example in which the predicted breathing sequence 3 is determined.

In this example a breathing rate 27 of the user 2 is measured and a breathing phase 29 of the user 2 is also measured. In some examples the predicted breathing sequence 3 is extrapolated from the measured breathing rate 27 and the measured breathing phase 29. In such an example the predicted breathing sequence 3 may have a regular period.

In other examples, the predicted breathing sequence 3 may take account of other factors which can influence the breathing sequence of the user 2. The predicted breathing sequence 3 may, for example, be based, at least in part, on an effect on the breathing rate and/or breathing phase of the user 2 which is predicted to result from the rendering of media content to the user 2 which precedes the rendering of the first media content 5.

In the example of FIG. 6, the predicted breathing sequence 3 is additionally based on a user profile 31. The user profile 31 is used to predict divergence of breathing phases of the user from breathing phases of different users over time based on media content.

The user profile 31 may, for example, comprise a user history which records how the user 2 has historically responded to different types of media content. Therefore, the predicted effect of media content which is rendered to the user 2 preceding the rendering of the first media content 5 may be predicted using the user profile 31. Since different users respond differently to different content, the corresponding user profiles will reflect this divergence in their historic responses. This will propagate through into predictions about future breathing phases that are based on the user profiles in view of the same media content to be rendered.

In some examples the effect may also be predicted based on responses by one or more other users to the preceding media content. The responses of the one or more other users to the preceding media content may be mapped to the predicted effect on the present user 2 based on a comparison between the historic response of the present user 2 and a historic response of the one or more other users to commonly consumed other media content.

The user profile 31 may comprise data indicative of the mood of the user 2 and/or the environment in which the user 2 will receive the first media content 5.

In the example of FIG. 6, the predicted breathing sequence 3 is determined by the apparatus 1 based on inputs comprising the measured breathing rate 27 of the user 2, the measured breathing phase 29 of the user 2 and the respective user profile 31. However, it is to be appreciated that these inputs could be remotely processed at a remote device to obtain the predicted breathing sequence 3 which is subsequently communicated to the apparatus 1.

Figure 7:
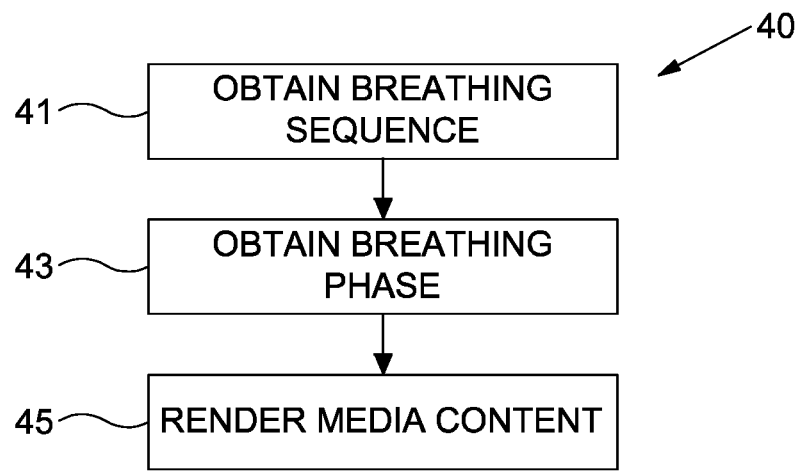
FIG. 7 shows an example of a method as described herein.

FIG. 7 illustrates an example of a method 40 for causing improved temporal alignment of the first media content 5 with the desired breathing phase 7 for consuming the first media content 5.

In block 41 of the method 40, the predicted breathing sequence of the user 2 is obtained.

In some examples, the predicted breathing sequence 3 is obtained in block 41 by processing the measured breathing rate 27 of the user 2 and the measured breathing phase 29 of the user 2 in a manner as described in relation to FIG. 6.

In some examples the predicted breathing sequence 3 is obtained in block 41 by using the user profile 31 to predict divergence of breathing phase of different users over time based on media content in a manner as described in relation to FIG. 6.

In block 43 of the method 40, the desired breathing phase 7 for consuming the first media content 5 is obtained.

In some examples, block 43 comprises obtaining at least the first media content 5 and obtaining metadata which tags specific media content so that the specific media content is associated with a particular desired breathing phase. Using the metadata, the first media content 5 can be associated with the particular desired breathing phase 7.

In other examples the desired breathing phase 7 for consuming the media content 5 is obtained in block 43 by analysis and classification of features of the first media content 5.

In some examples, the desired breathing phase 17 for consuming the second media content 15 is also obtained in block 43. The desired breathing phase 17 may also be obtained using the metadata or by analysis and classification of features of the second media content 15.

In block 45 of the method 40, rendering of the first media content 5 to the user 2 at the first time $t_1$ is caused, wherein the first time $t_1$ is based, at least in part, on the predicted time in the predicted breathing sequence 3 at which the desired breathing phase 7 occurs.

In some examples, causing rendering of the first media content 5 to the user 2 at the first time $t_1$ in block 45 comprises controlling a delay 9 between an input 11 to trigger rendering of the first media content 5 and rendering of the first media content 5 at the first time $t_1$ in a manner as described in relation to FIG. 3.

In some examples, causing rendering of the first media content 5 to the user 2 at the first time $t_1$ in block 45 comprises controlling the temporal relationship between the first media content 5 and the second media content 15 which precedes the first media content 5 in the sequence of rendering 19 in a manner as described in relation to FIGS. 4A to 4E. The temporal relationship between the first media content 5 and the second media content 15 may be controlled to minimize a difference measure in a manner as described in relation to FIG. 5.

While, in the foregoing description, the rendering of the first media content 5 to the user 2 has been described as being controlled so as to improve temporal alignment of the rendering of the first media content 5 to the user 2 with the corresponding desired breathing phase 7, additionally or alternatively, the apparatus 1 can cause a changed breathing sequence to achieve or improve the temporal alignment of the rendering of the first media content 5 and the corresponding desired breathing phase 7.

Figure 8:
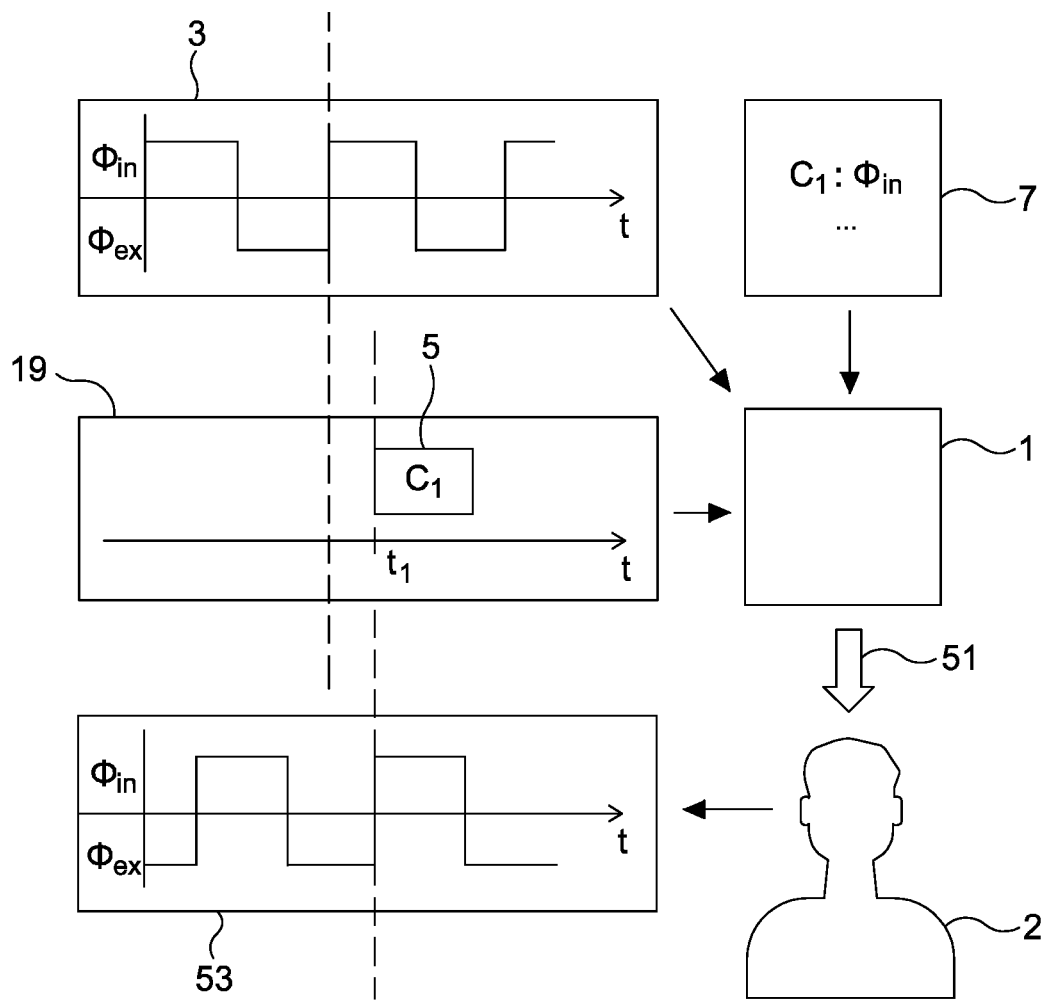
FIG. 8 shows another example of an apparatus as described herein.

FIG. 8 schematically illustrates an example of the apparatus 1 causing a changed breathing sequence 53 to achieve or improve the temporal alignment of the rendering of the first media content 5 and the corresponding desired breathing phase 7.

In FIG. 8, the apparatus 1 obtains the predicted breathing sequence 3 of the user 2 and obtains the first time $t_1$ when it is predicted that the first media content 5 will be rendered to the user 2. In some examples obtaining the first time $t_1$ comprises obtaining a determined sequence of rendering 19 of media content including the first media content 5. In other examples obtaining the first time $t_1$ comprises obtaining an original timeline 13 associated with the first media content 5, for example via metadata associated with the first media content 5. The apparatus 1 also obtains the desired breathing phase 7 for consuming the first media content 5.

The apparatus 1 causes at least one stimulus 51 to be provided to the user 2. The at least one stimulus 51 is configured to cause a changed breathing sequence 53 instead of the predicted breathing sequence 3. The changed breathing sequence 53 is such that the desired breathing phase 7 in the changed breathing sequence 53 is temporally shifted towards the first time $t_1$, at which the first media content 5 will be rendered to the user 2, as compared to the desired breathing phase 7 in the predicted breathing sequence 3.

In some examples the at least one stimulus 51 comprises at least one from an audio, visual, or haptic output to the user 2. The apparatus 1 may be configured to control or produce one or more of said outputs.

Figure 9:
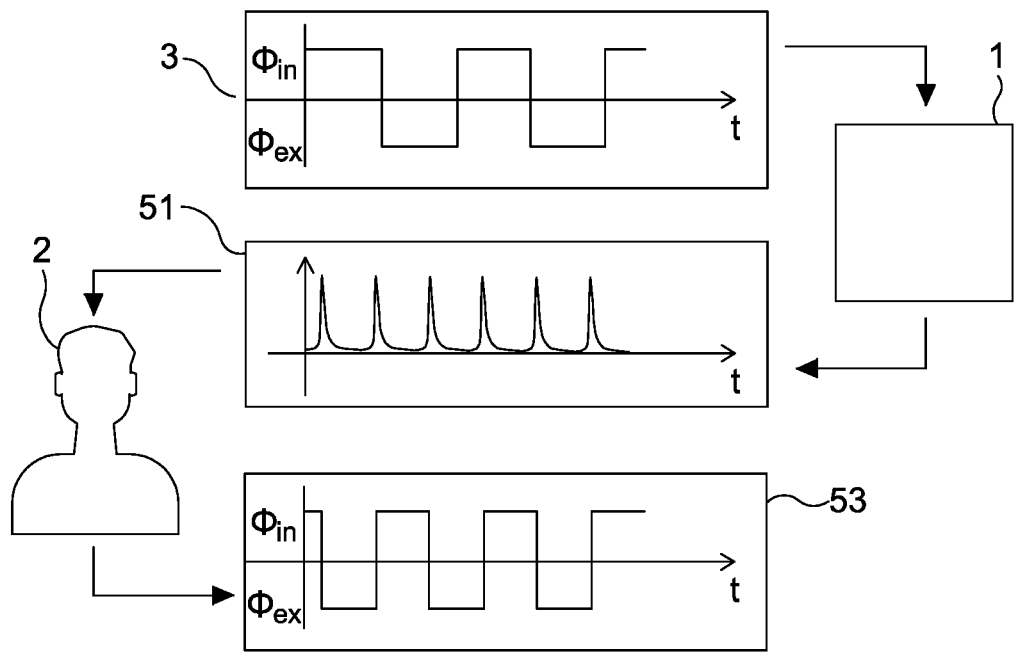
FIG. 9 shows an example of a stimulus to cause a changed breathing sequence as described herein.

FIG. 9 schematically illustrates an example of at least one stimulus 51 which may be provided to the user 2 in order to cause the changed breathing sequence 53. In this example, the at least one stimulus 51 has a tempo configured to entrain the breathing sequence of the user 2 to thereby cause the changed breathing sequence 53.

In some examples the tempo may not be a constant tempo but may change over time in order to effect both entrainment and the changed breathing sequence 53. For example, the tempo initially of the at least one stimulus 51 may diverge slightly from the tempo of the breathing sequence of the user 2 at the beginning. Over time, as the breathing sequence of the user 2 becomes entrained with the at least one stimulus 51, the tempo of the at least one stimulus 51 may be adjusted further towards the tempo of the changed breathing sequence 53 that is targeted. In this manner the breathing sequence of the user 2 is gradually changed towards the changed breathing sequence 53 that is targeted, becoming entrained with the at least one stimulus 51 at various different tempos in the process.

In some examples the at least one stimulus 51 comprises a mindfulness breathing prompt in which the phase and tempo are controlled to entrain the breathing sequence of the user 2. In such examples the phases of the prompt, for example a waxing phase and a waning phase, may be correlated with targeted inhaling phases and exhaling phases respectively in the changed breathing sequence 53 that is targeted. In other examples the at least one stimulus 51 may comprise algorithmically selected or generated music having a tempo which is configured to entrain the breathing sequence of the user 2 to thereby cause the changed breathing sequence 53. In other examples the at least one stimulus 51 may comprise algorithmically generated speech in which the prosody and timing is controlled to entrain the breathing sequence of the user 2 to thereby cause the changed breathing sequence 53.

Figure 10:
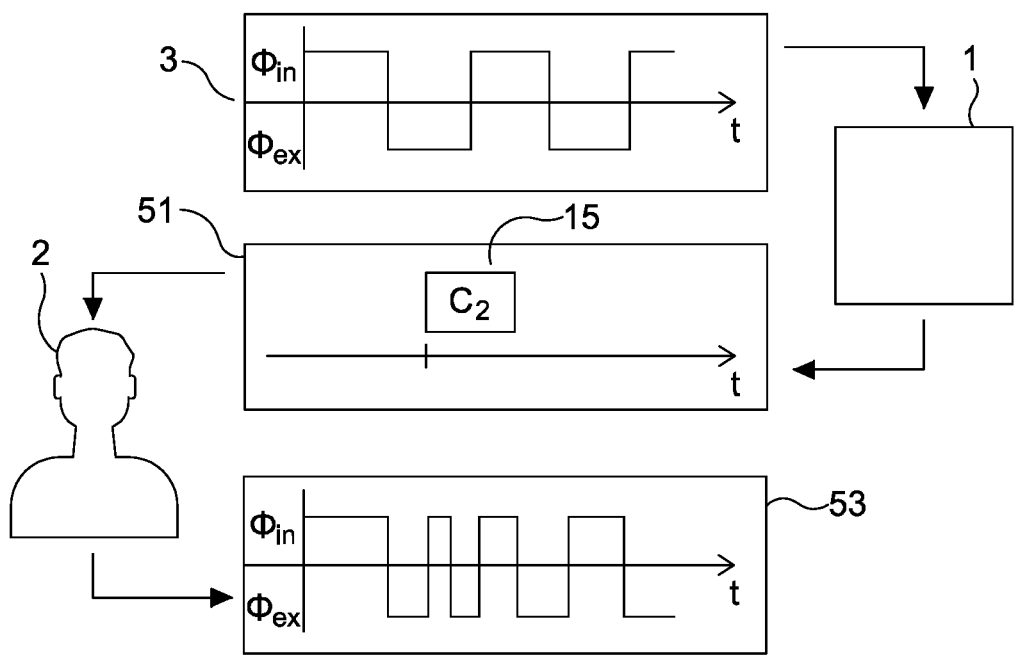
FIG. 10 shows another example of a stimulus to cause a changed breathing sequence as described herein.

FIG. 10 schematically illustrates another example of at least one stimulus 51 which is configured to cause the changed breathing sequence 53. In this example, the at least one stimulus 51 provided to a user 2 comprises rendering a second media content 15 to the user 2 prior to rendering the first media content 5 to the user. In this example, the second media content 15 is determined to be a media content which will, at least in part, cause the changed breathing sequence 53. For example, the second media content 15 is a media content which is predicted to have an effect on the breathing sequence of the user 2 which causes a changed breathing sequence 53 in which the desired breathing phase 7 for consuming the first media content 5 is temporally aligned or more closely temporally aligned with the first time $t_1$ of rendering of the first media content 5. For example, the second media content 15 may be a media content which is predicted to cause a sharp intake of breath or to quicken, at least temporarily, a breathing rate of the user 2.

Figure 11:
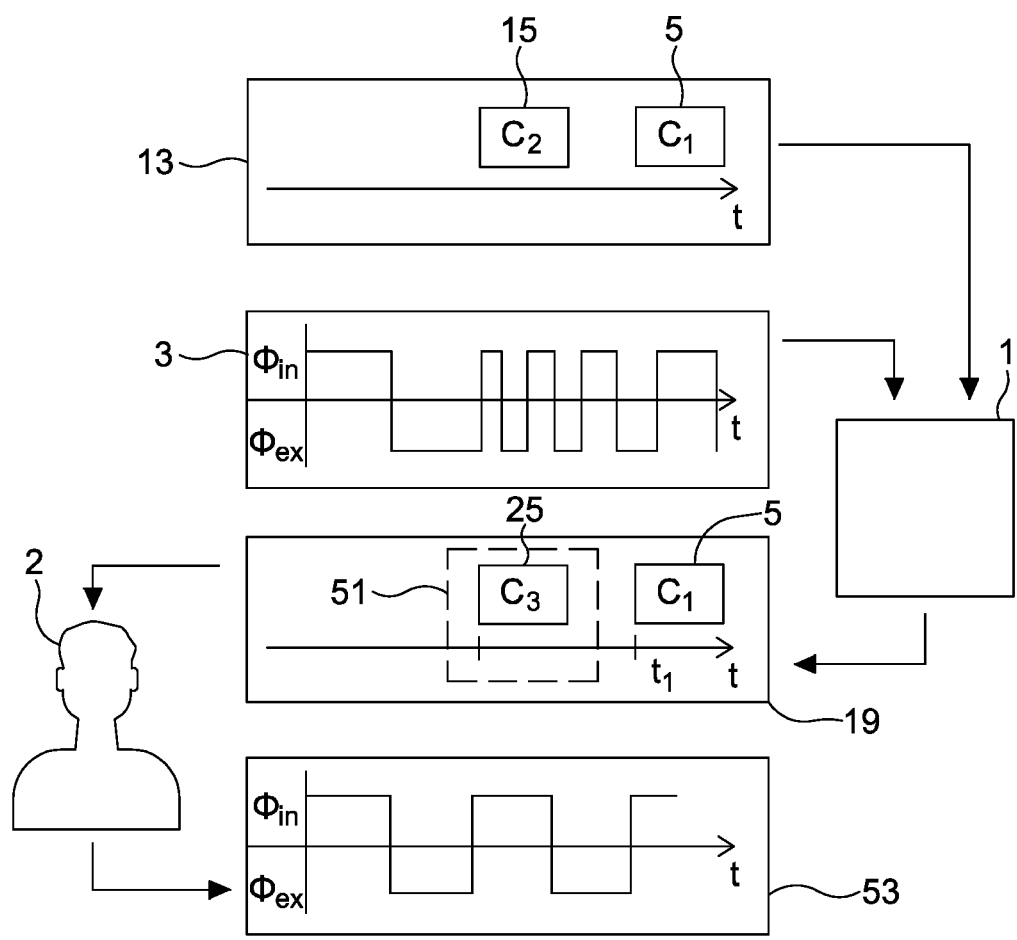
FIG. 11 shows another example of a stimulus to cause a changed breathing sequence as described herein.

In some examples, as schematically illustrated in FIG. 11, the second media content 15 is rendered to the user 2 instead of a third media content 25 which precedes the first media content 5 in the original timeline 13. The predicted effect, on the user 2, of consuming the third media content 25 is replaced with the effect, on the user 2, of consuming the second media content 15.

The predicted breathing sequence 3 is determined accounting for the predicted effect of the third media content 25. Therefore, as a result of replacing the third media content 25 with the second media content 15, the changed breathing sequence 53 will be caused instead of the predicted breathing sequence 3.

Figure 12:
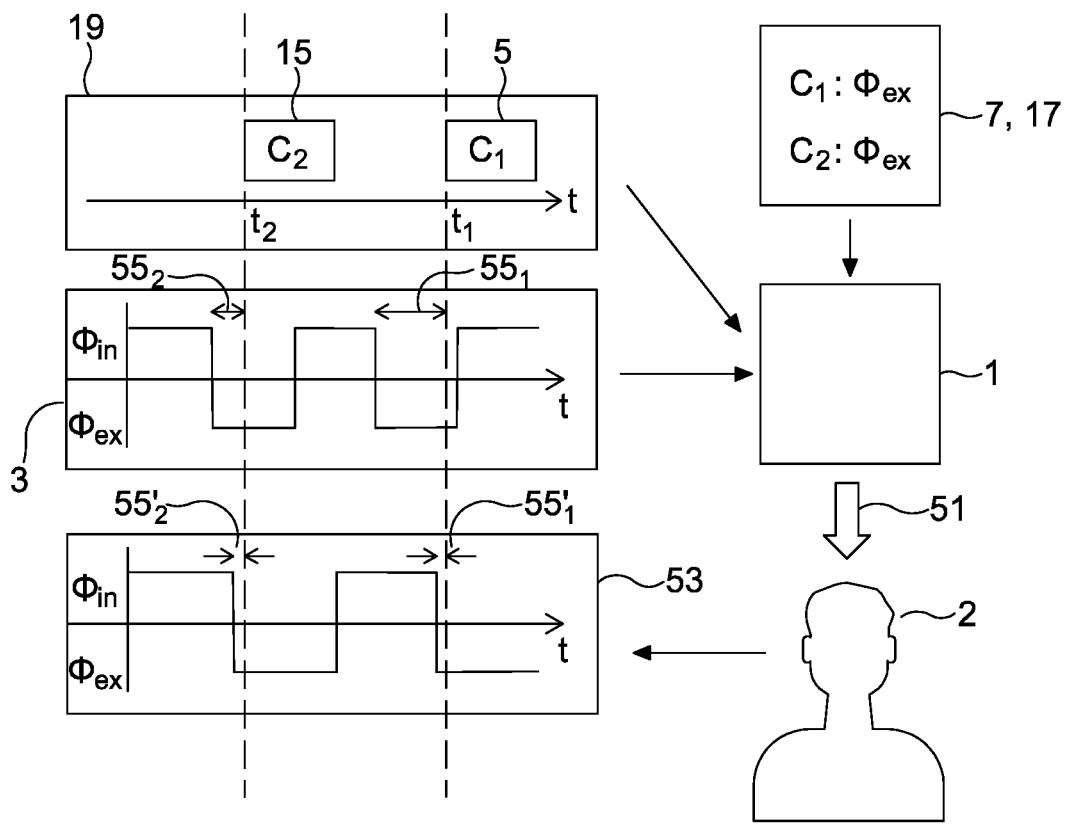
FIG. 12 shows an example of determining a changed breathing sequence as described herein.

FIG. 12 schematically illustrates an example of how the apparatus 1 can cause a changed breathing sequence 53 which minimizes a difference measure between media content, such as the first media content 5 and the second media content 15, and corresponding desired breathing phases, such as desired breathing phase 7 for consuming the first media content 5 and desired breathing phase 17 consuming the second media content 15.

In this example, the apparatus 1 obtains the desired breathing phase 7 for consuming the first media content 5 and the desired breathing phase 17 for consuming the second media content 15.

The apparatus 1 compares a predicted time in the predicted breathing sequence 3 at which the desired breathing phase 7 occurs with the first time $t_1$ of rendering the first media content 5 in the sequence of rendering 19 to obtain a difference $55_1$. Likewise, the apparatus 1 compares a predicted time in the predicted breathing sequence 3 at which the desired breathing phase 17 occurs with a second time $t_2$ of rendering the second media content 15 in the sequence of rendering 19 to obtain a difference $55_2$.

These differences $55_1$, $55_2$ between the times $t_1$, $t_2$ of rendering the first and second media content 5, 15 in the sequence of rendering 19 and the predicted times of the desired breathing phases 7, 17 in the predicted breathing sequence 3 are used to determine a difference measure.

The apparatus 1 causes the at least one stimulus 51 to be provided to the user to thereby cause the changed breathing sequence 53 which minimize the difference measure.

The changed breathing sequence 53 results in the user 2 having the desired breathing phase 7 at a time which differs from the first time $t_1$, at which the first media content 5 is rendered to the user 2, by a difference $55_1'$. The change breathing sequence 53 results in the user 2 having the desired breathing phase 17 at a time which differs from a second time $t_2$, at which the second media content 15 is rendered to the user 2, by a difference $55_2'$.

In the example of FIG. 12 it can be seen that the at least one stimulus 51 has induced a slower rate of breathing in the changed breathing sequence 53 as compared to the predicted breathing sequence 3. As a result, the overall temporal deviation of the rendering of the first and second media content 5, 15 from corresponding desired breathing phases 7, 17 is reduced, though it is to be appreciated that individually the differences $55_1'$ and $55_2'$ may not each be reduced as compared to the differences $55_1$ and $55_2$.

The difference measure may be a cost function. The difference measure may be minimized in the presence of constraints. The constraints may be soft constraints or hard constraints or a mixture of both.

Soft constraints may include the extent to which the at least one stimulus 51, which is required to cause the particular changed breathing sequence 53, is perceived to be intrusive to the user 2. The perceived intrusiveness may be determined based on a historic response of the present user to such stimuli or the responses of other users to such stimuli. The particular changed breathing sequence 53 may be penalized in the difference measure to an extent commensurate with the extent to which the at least one stimulus 51, which is required to cause the particular changed breathing sequence 53, is perceived to be intrusive to the user 2.

Soft constraints may involve weighting different media content differently based on an importance of temporally aligning the rendered media content with the corresponding desired breathing phase in view of achieving the overall goal of rendering the media content associated with the original timeline 13.

Hard constraints may involve requiring temporal alignment of a certain one or more media content with a corresponding desired breathing phase where the importance exceeds a threshold condition.

Figure 13:
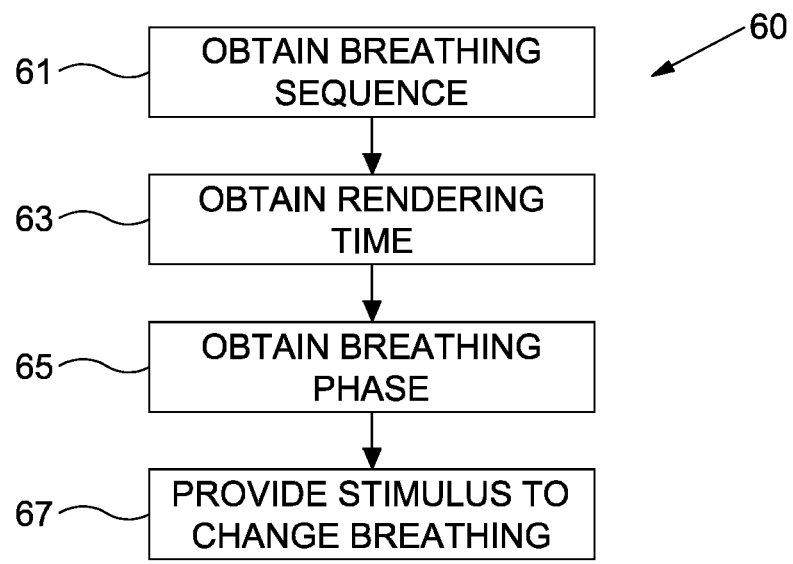
FIG. 13 shows another example of a method as described herein.

FIG. 13 illustrates an example of a method 60 for causing the changed breathing sequence 53 to achieve or improve temporal alignment of the rendering of the first media content 5 and the corresponding desired breathing phase 7.

In block 61 of the method 60, the predicted breathing sequence 3 of the user 2 is obtained as per block 41 of method 40.

This may involve, for example, processing the measured breathing rate 27 and measured breathing phase 29 of the user 31 and using the user profile 31 to predict divergence of breathing phase of different users over time based on media content.

In block 63 of the method 60, the first time $t_1$ when it is predicted that the first media content 5 will be rendered to the user 2 is obtained in a manner as described in relation to FIG. 8.

In block 65 of the method 60, the desired breathing phase 7 for consuming the first media content 5 is obtained as per block 43 of method 40.

The desired breathing phase 17 for consuming the second media content 15 may also be obtained in block 65.

The desired breathing phases 7, 17 may be obtained using metadata which tags specific media content so that the specific media content is associated with a particular desired breathing phase or by analysis and classification of features of, respectively, the first and second media content 5, 15.

In block 67 of the method 60, the at least one stimulus 51 is caused to be provided to the user 2, wherein the at least one stimulus 51 is configured to cause the changed breathing sequence 53 instead of the predicted breathing sequence 3, and wherein the desired breathing phase 7 in the changed breathing sequence 53 is temporally shifted towards the first time $t_1$ as compared to the desired breathing phase 7 in the predicted breathing sequence 3.

The at least one stimulus 51 can have a tempo which is configured to entrain a breathing sequence of the user 2 to thereby cause the changed breathing sequence 53 and/or may involve rendering the second media content 15 to the user 2 prior to the first media content 5 and, in some examples, in place of the third media content 25 which precedes the first media content 5 in the original timeline 13.

The changed breathing sequence 53 can be determined such that it minimizes a difference measure in a manner as described in relation to FIG. 12.

Figure 14:
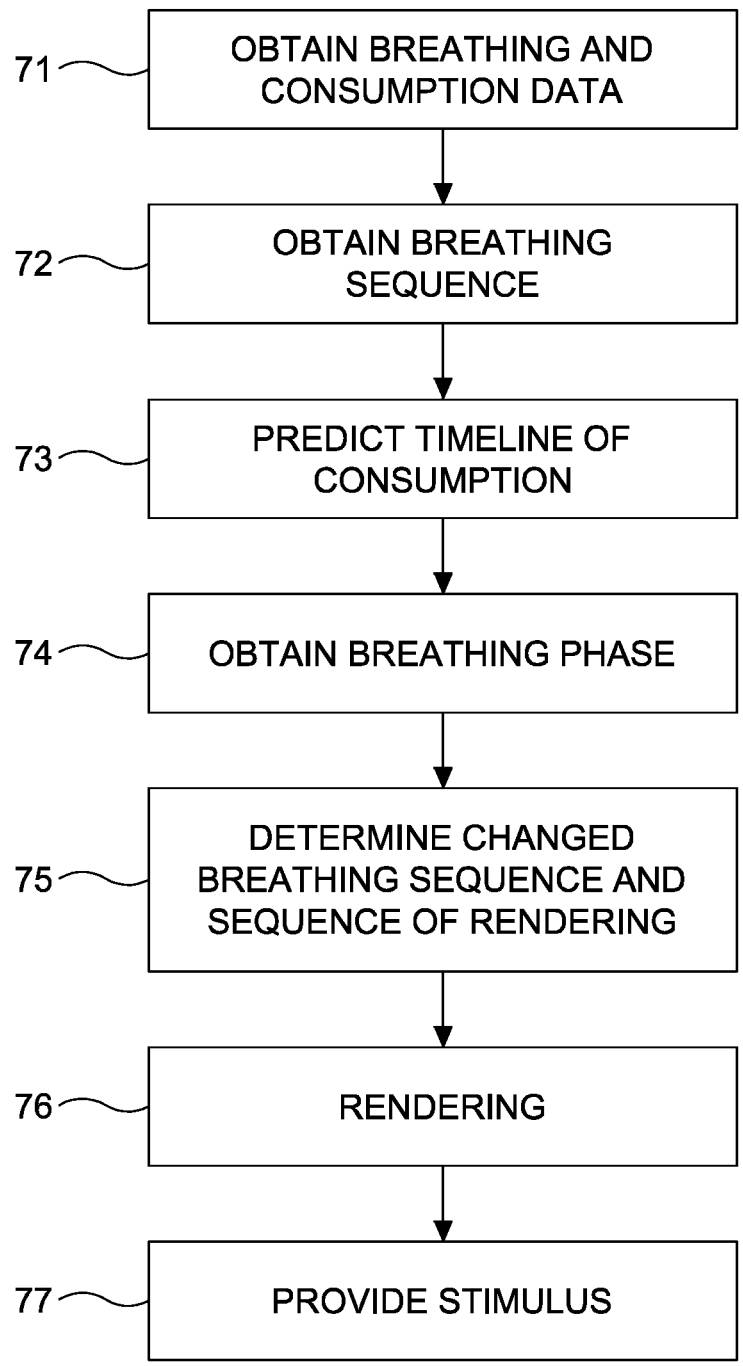
FIG. 14 shows another example of a method as described herein.

FIG. 14 illustrates an example of a method 70 in which both the breathing sequence of the user 2 may be changed using the provision of at least one stimulus 51 and the time $t_1$ of rendering the first media content 5 to the user 2 may be changed.

In block 71 of the method 70, the breathing rate and phase of the user 2 are measured so as to obtain the measured breathing rate 27 and measured breathing phase 29. The rate of consumption of media content by the user 2 is also measured.

In block 72 of the method 70, the predicted breathing sequence 3 of the user 2 is obtained as per block 41 of method 40 and block 61 of method 60.

In block 73 of the method 70, a predicted timeline of consumption of the first media content 5 is determined based on the original timeline 13 associated with the first media content 5 and the rate of consumption of the media content by the user 2.

In some examples, the predicted timeline of consumption is also based on predicted fluctuations in the rate of consumption of the media content by the user 2. These fluctuations may be predicted based on the media content. For example, the fluctuations can be predicted based upon the rate at which the user 2 has, historically, consumed similar media content. In other examples the fluctuations can be predicted based upon the rate at which one or more other users have consumed the media content.

In block 74 of method 70, the desired breathing phase 7 for consuming the first media content 5 is obtained as per block 43 in method 40 and block 65 of method 60.

In some examples, block 74 comprises determination of one or more of emotional tone, meaning, comprehension importance of the first media content 5, or goals of the first media content 5 such as education, relaxation, etc. The determination may be achieved by reading metadata associated with the first media content 5 or by analysis and classification of features of the first media content 5. The analysis may involve, for example, key word density analysis or audio profile analysis as described in the foregoing. The analysis can be performed by a pre-trained machine learning algorithm.

The desired breathing phase 7 of the first media content 5 can be obtained in block 94 by determining which breathing phase is most appropriate in view of the determined emotional tone, meaning, comprehension importance of the first media content 5, and/or goals of the first media content 5 such as education, relaxation, etc. For example, where the first media content 5 is a sentence which is designed to be surprising, the desired breathing phase 7 for consuming this sentence may be determined to be an early phase of inhalation, which is known to augment excitement.

In block 75 of the method 70, there is determined a combination of a changed breathing sequence 53 and a sequence of rendering 19 that improve the temporal alignment of the first media content 5 and the desired breathing phase 7 for consuming the first media content 5.

A combination is determined that minimizes a difference measure in respect of the time of rendering the first media content 5 in the sequence of rendering 19 and the predicted time at which the desired breathing phase 7 occurs in the changed breathing sequence 53.

The minimization of the difference measure may be constrained by, for example, penalization of intrusiveness of the at least one stimulus 51 to cause the changed breathing sequence 53 and penalization of the noticeability of the changes to the sequence of rendering 19 as compared to what the user 2 would expect. The extent of the penalization in the difference measure is commensurate with the extent to which the achievement of the changed breathing sequence 53 and sequence of rendering 19 is intrusive and noticeable.

The combination determined in block 75 is implemented by causing rendering of the sequence 19 to the user 2 in block 76 of the method 70, and by causing provision of the at least one stimulus 51 which causes the changed breathing sequence 53 to be provided to the user 2 In block 77 of the method 70.

FIG. 15A illustrates an example of a controller 81. The controller 81 may function as the apparatus 1 or may be comprised within the apparatus 1.

Implementation of a controller 81 may be as controller circuitry. The controller 81 may be implemented in hardware alone, have certain aspects in software including firmware alone or can be a combination of hardware and software (including firmware).

As illustrated in FIG. 15A the controller 81 may be implemented using instructions that enable hardware functionality, for example, by using executable instructions of a computer program 87 in a general-purpose or special-purpose processor 83 that may be stored on a computer readable storage medium (disk, memory etc.) to be executed by such a processor 83.

The processor 83 is configured to read from and write to the memory 85. The processor 83 may also comprise an output interface via which data and/or commands are output by the processor 83 and an input interface via which data and/or commands are input to the processor 83.

The memory 85 stores a computer program 87 comprising computer program instructions (computer program code) that controls the operation of the apparatus 1 when loaded into the processor 83. The computer program instructions, of the computer program 87, provide the logic and routines that enables the apparatus to perform the methods illustrated in FIGS. 7, 13 and 14. The processor 83 by reading the memory 85 is able to load and execute the computer program 87.

The apparatus 1 therefore comprises:
at least one processor 83; and
at least one memory 85 including computer program code
the at least one memory 85 and the computer program code configured to, with the at least one processor 83, cause the apparatus 1 at least to perform:
obtaining a predicted breathing sequence 3 of a user 2;
obtaining a desired breathing phase 7 for consuming a first media content 5; and
causing rendering of the first media content 5 to the user 2 at a first time $t_1$ which is based, at least in part, on a predicted time in the predicted breathing sequence 3 at which the desired breathing phase 7 occurs.

Additionally or alternatively, the at least one memory 85 and the computer program code are configured to, with the at least one processor 83, cause the apparatus 1 to perform:
obtaining a predicted breathing sequence 3 of a user 2;
obtaining a first time $t_1$ when it is predicted that a first media content 5 will be rendered to the user 2;
obtaining a desired breathing phase 7 for consuming the first media content 5; and causing at least one stimulus 51 to be provided to the user 2, the at least one stimulus 51 configured to cause a changed breathing sequence 53 instead of the predicted breathing sequence 3, wherein the desired breathing phase 7 in the changed breathing sequence 53 is temporally shifted towards the first time $t_1$ as compared to the desired breathing phase 7 in the predicted breathing sequence 3.

As illustrated in FIG. 15B, the computer program 87 may arrive at the apparatus 1 via any suitable delivery mechanism 89. The delivery mechanism 89 may be, for example, a machine readable medium, a computer-readable medium, a non-transitory computer-readable storage medium, a computer program product, a memory device, a record medium such as a Compact Disc Read-Only Memory (CD-ROM) or a Digital Versatile Disc (DVD) or a solid state memory, an article of manufacture that comprises or tangibly embodies the computer program 87. The delivery mechanism may be a signal configured to reliably transfer the computer program 87. The apparatus 1 may propagate or transmit the computer program 87 as a computer data signal.

Computer program instructions for causing an apparatus to perform at least the following or for performing at least the following:

obtaining a predicted breathing sequence 3 of a user 2;

obtaining a desired breathing phase 7 for consuming a first media content 5; and causing rendering of the first media content 5 to the user 2 at a first time $t_1$ which is based, at least in part, on a predicted time in the predicted breathing sequence 3 at which the desired breathing phase 7 occurs.

Additionally or alternatively, the computer program instructions are for causing an apparatus to perform at least the following or for performing at least the following:

obtaining a predicted breathing sequence 3 of a user 2;

obtaining a first time $t_1$ when it is predicted that a first media content 5 will be rendered to the user 2;

obtaining a desired breathing phase 7 for consuming the first media content 5; and causing at least one stimulus 51 to be provided to the user 2, the at least one stimulus 51 configured to cause a changed breathing sequence 53 instead of the predicted breathing sequence 3, wherein the desired breathing phase 7 in the changed breathing sequence 53 is temporally shifted towards the first time $t_1$ as compared to the desired breathing phase 7 in the predicted breathing sequence 3.

The computer program instructions may be comprised in a computer program, a non-transitory computer readable medium, a computer program product, a machine readable medium. In some but not necessarily all examples, the computer program instructions may be distributed over more than one computer program.

Although the memory 85 is illustrated as a single component/circuitry it may be implemented as one or more separate components/circuitry some or all of which may be integrated/removable and/or may provide permanent/semi-permanent/dynamic/cached storage.

Although the processor 83 is illustrated as a single component/circuitry it may be implemented as one or more separate components/circuitry some or all of which may be integrated/removable. The processor 83 may be a single core or multi-core processor.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' may refer to one or more or all of the following:

(a) hardware-only circuitry implementations (such as implementations in only analog and/or digital circuitry) and (b) combinations of hardware circuits and software, such as (as applicable):

(i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions and (c) hardware circuit(s) and or processor(s), such as a microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor and its (or their) accompanying software and/or firmware. The term circuitry also covers, for example and if applicable to the particular claim element, a baseband integrated circuit for a mobile device or a similar integrated circuit in a server, a cellular network device, or other computing or network device.

The blocks illustrated in the FIGS. 7, 13 and 14 may represent steps in a method and/or sections of code in the computer program 87. The illustration of a particular order to the blocks does not necessarily imply that there is a required or preferred order for the blocks and the order and arrangement of the block may be varied. Furthermore, it may be possible for some blocks to be omitted.

The apparatus 1 of FIG. 1 may be or may comprise the controller 81 of FIG. 15A or may be any computer or machine capable of reading the computer program 87 from the delivery mechanism 89 of FIG. 15B and running that computer program 87.

FIG. 16 schematically illustrates a device 91 comprising the controller 81 of FIG. 15A.

The device 91 comprises at least one breathing sensor 93 configured to enable the predicted breathing sequence of the user to be obtained. For example, the at least one breathing sensor 93 may be configured to monitor the parameters of the breathing activity of the user 2, such as breathing rate and breathing phase. These parameters may be measured and recorded in, for example, the memory 85 or remotely in a Cloud.

In some examples the at least one breathing sensor 93 comprises a front facing camera or microphone or other sensing apparatus.

The device 91 also comprises at least one user interface 95 configured to render media content such as the first media content 5 to the user 2.

The at least one user interface 95 can also be used to provide the at least on stimulus 51 to the user 2 to cause the changed breathing sequence 53.

The at least one user interface 95 can also be used to monitor the rate of consumption of media content by the user 2. For example, where the at least one user interface 95 comprises a display, it can be used to monitor the scrolling rate of the user 2.

The at least one user interface 95 may comprise one or more from a display, a speaker, or other types of user interface.

The device 91 may comprise further sensors (not shown) which may enable determination of contextual information such as the location of the device 91, the time of day, the mood of the user 2, etc.

In some examples the device 91 is an electronic device. The electronic device may be a portable electronic device such as a handheld electronic device or a wearable electronic device. The device 91 may be configured for mobile cellular communication. The device may be a smartphone, a smartwatch, or another type of portable media player.

The apparatus 1 of FIG. 1 may be or may comprise the device 91 of FIG. 16.

It is to be appreciated that the apparatus 1 may comprise any suitable means for performing the functions hereinbefore described.

Consequently, in some examples, the apparatus 1 comprises means for:

obtaining a predicted breathing sequence 3 of a user 2;

obtaining a desired breathing phase 7 for consuming a first media content 5; and causing rendering of the first media content 5 to the user 2 at a first time $t_1$ which is based, at least in part, on a predicted time in the predicted breathing sequence 3 at which the desired breathing phase 7 occurs.

Additionally or alternatively, the apparatus 1 comprises means for:

obtaining a predicted breathing sequence 3 of a user 2;

obtaining a first time $t_1$ when it is predicted that a first media content 5 will be rendered to the user 2;

obtaining a desired breathing phase 7 for consuming the first media content 5; and causing at least one stimulus 51 to be provided to the user 2, the at least one stimulus 51 configured to cause a changed breathing sequence 53 instead of the predicted breathing sequence 3, wherein the desired breathing phase 7 in the changed breathing sequence 53 is temporally shifted towards the first time $t_1$ as compared to the desired breathing phase 7 in the predicted breathing sequence 3.

Where a structural feature has been described, it may be replaced by means for performing one or more of the functions of the structural feature whether that function or those functions are explicitly or implicitly described.

In some but not necessarily all examples, the apparatus 1 is configured to communicate data from the apparatus 1 with or without local storage of the data in a memory 85 at the apparatus 1 and with or without local processing of the data by circuitry or processors at the apparatus 1.

The data may, for example, be the measured breathing rate 27, the measured breathing phase 29, the user profile 31 or data that can be used to augment the user profile 31, the first and second media content 5, 15, the rate of consumption of media content by the user 2, etc.

The data may be stored in processed or unprocessed format remotely at one or more devices.

The data may be stored in the Cloud.

The data may be processed remotely at one or more devices. The data may be partially processed locally and partially processed remotely at one or more devices.

Subsequent to processing of the aforementioned data at the remote device(s), the apparatus 1 may receive, from the remote device(s), for example: the predicted breathing phase 3; the desired breathing phases 7, 17; metadata associated with the first and second media content 5, 15; data indicative of an emotional tone, meaning, comprehension importance of the first and second media content 5, 15, and/or goals of the first and second media content 5, 15 such as education, relaxation, etc.; a predicted timeline of consumption of the first media content 5; etc.

The data may be communicated to the remote devices wirelessly via short range radio communications such as Wi-Fi or Bluetooth, for example, or over long range cellular radio links. The apparatus may comprise a communications interface such as, for example, a radio transceiver for communication of data.

The apparatus 1 may be part of the Internet of Things forming part of a larger, distributed network.

The processing of the data, whether local or remote, may be for the purpose of health monitoring, data aggregation, patient monitoring, vital signs monitoring or other purposes. For example, the measured breathing rate and phase 27, 29 of the user 2 may be monitored for both health-related purposes and for improving models of user responses to particular media content, which can be used to improve the algorithms used to improve temporal alignment between the rendering of media content and a corresponding desired breathing phase for consuming the media content in the future.

The processing of the data, whether local or remote, may involve artificial intelligence or machine learning algorithms. The data may, for example, be used as learning input to train a machine learning network or may be used as a query input to a machine learning network, which provides a response. The machine learning network may for example use linear regression, logistic regression, vector support machines or an acyclic machine learning network such as a single or multi hidden layer neural network.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this description, reference has been made to various examples. The description of features or functions in relation to an example indicates that those features or functions are present in that example. The use of the term 'example' or 'for example' or 'can' or 'may' in the text denotes, whether explicitly stated or not, that such features or functions are present in at least the described example, whether described as an example or not, and that they can be, but are not necessarily, present in some of or all other examples. Thus 'example', 'for example', 'can' or 'may' refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example as part of a working combination but does not necessarily have to be used in that other example.

Although embodiments have been described in the preceding paragraphs with reference to various examples, it should be appreciated that modifications to the examples given can be made without departing from the scope of the claims.

Features described in the preceding description may be used in combinations other than the combinations explicitly described above.

Although functions have been described with reference to certain features, those functions may be performable by other features whether described or not.

Although features have been described with reference to certain embodiments, those features may also be present in other embodiments whether described or not.

The term 'a' or 'the' is used in this document with an inclusive not an exclusive meaning. That is any reference to X comprising a/the Y indicates that X may comprise only one Y or may comprise more than one Y unless the context clearly indicates the contrary. If it is intended to use 'a' or 'the' with an exclusive meaning then it will be made clear in the context. In some circumstances the use of 'at least one' or 'one or more' may be used to emphasis an inclusive meaning but the absence of these terms should not be taken to infer and exclusive meaning.

The presence of a feature (or combination of features) in a claim is a reference to that feature or (combination of features) itself and also to features that achieve substantially the same technical effect (equivalent features). The equivalent features include, for example, features that are variants and achieve substantially the same result in substantially the same way. The equivalent features include, for example, features that perform substantially the same function, in substantially the same way to achieve substantially the same result.

In this description, reference has been made to various examples using adjectives or adjectival phrases to describe characteristics of the examples. Such a description of a characteristic in relation to an example indicates that the characteristic is present in some examples exactly as described and is present in other examples substantially as described.

Whilst endeavoring in the foregoing specification to draw attention to those features believed to be of importance it should be understood that the Applicant may seek protection via the claims in respect of any patentable feature or combination of features hereinbefore referred to and/or shown in the drawings whether or not emphasis has been placed thereon.

We claim:

1. An apparatus comprising:
   at least one processor; and
   at least one memory including computer program code, the at least one memory and the computer program code configured to, with the at least one processor, cause the apparatus at least to perform:
   obtaining a predicted breathing sequence of a user;
   obtaining a first time when it is predicted that a first media content will be rendered to the user;
   obtaining a desired breathing phase for consuming the first media content; and
   causing at least one stimulus to be provided to the user, the at least one stimulus configured to cause a changed breathing sequence instead of the predicted breathing sequence,
   wherein the desired breathing phase in the changed breathing sequence is temporally shifted towards the first time as compared to the desired breathing phase in the predicted breathing sequence.

2. An apparatus as claimed in claim 1, wherein the at least one stimulus comprises at least one of an audio, visual, haptic output to the user.

3. An apparatus as claimed in claim 1, wherein the at least one stimulus has a tempo configured to entrain a breathing sequence of the user to cause the changed breathing sequence.

4. An apparatus as claimed in claim 1, wherein causing the at least one stimulus to be provided to the user comprises rendering a second media content to the user prior to the first media content, the second media content being determined to at least partially cause the changed breathing sequence.

5. An apparatus as claimed in claim 4, wherein the second media content is rendered to the user instead of a third media content, wherein the third media content precedes the first media content in an original timeline.

6. An apparatus as claimed in claim 1, wherein the at least one memory and the computer program code configured to, with the at least one processor, cause the apparatus at least to perform: obtaining a desired breathing phase for consuming another media content comprised in a sequence comprising the first media content; determining a difference measure between the first media content and the another media content with respect to the corresponding desired breathing phases; and determining the changed breathing sequence to minimize the difference measure.

7. An apparatus as claimed in claim 1, wherein the predicted breathing sequence is based, at least in part, on a measured breathing rate of the user and a measured breathing phase of the user.

8. An apparatus as claimed in claim 1, wherein the predicted breathing sequence is based, at least in part, on a user profile, wherein the user profile is used to predict divergence of breathing phases of the user from breathing phases of different users over time based on media content.

9. An apparatus as claimed in claim 1, wherein obtaining the desired breathing phase for consuming a first media content comprises reading metadata associated with the first media content.

10. An apparatus as claimed in claim 1, wherein, based on the first media content, the desired breathing phase for consuming a first media content is either an inhalation breathing phase of the user or an exhalation breathing phase of the user.

11. An apparatus as claimed in claim 1, comprising at least one breathing sensor configured to enable the predicted breathing sequence of the user to be obtained; and at least one user interface configured to provide the at least one stimulus to the user.

12. A method comprising:
    obtaining a predicted breathing sequence of a user;
    obtaining a first time when it is predicted that a first media content will be rendered to the user;
    obtaining a desired breathing phase for consuming the first media content; and
    causing at least one stimulus to be provided to the user, the at least one stimulus configured to cause a changed breathing sequence instead of the predicted breathing sequence,
    wherein the desired breathing phase in the changed breathing sequence is temporally shifted towards the first time as compared to the desired breathing phase in the predicted breathing sequence.

13. A method as claimed in claim 12, comprising obtaining at least the first media content and obtaining metadata which tags specific media content so that the specific media content is associated with a particular desired breathing phase.

14. A method as claimed in claim 12, wherein causing the at least one stimulus to be provided to the user comprises rendering a second media content to the user prior to the first media content, the second media content being determined to at least partially cause the changed breathing sequence.

15. A method as claimed in claim 14, wherein the second media content is rendered to the user instead of a third media content, wherein the third media content precedes the first media content in an original timeline.

16. A method as claimed in claim 12, comprising: obtaining a desired breathing phase for consuming another media content comprised in a sequence comprising the first media content; determining a difference measure between the first media content and the another media content with respect to the corresponding desired breathing phases; and determining the changed breathing sequence to minimize the difference measure.

17. A method as claimed in claim 12, wherein the predicted breathing sequence is based, at least in part, on a measured breathing rate of the user and a measured breathing phase of the user.

18. A method as claimed in claim 12, wherein the predicted breathing sequence is based, at least in part, on a user profile, wherein the user profile is used to predict divergence of breathing phases of the user from breathing phases of different users over time based on media content.

19. A non-transitory computer readable medium comprising program instructions stored thereon for performing at least the following:
   obtaining a predicted breathing sequence of a user;
   obtaining a first time when it is predicted that a first media content will be rendered to the user;
   obtaining a desired breathing phase for consuming the first media content; and
   causing at least one stimulus to be provided to the user, the at least one stimulus configured to cause a changed breathing sequence instead of the predicted breathing sequence,
   wherein the desired breathing phase in the changed breathing sequence is temporally shifted towards the first time as compared to the desired breathing phase in the predicted breathing sequence.

20. A non-transitory computer readable medium as claimed in claim 19, comprising program instructions stored thereon for performing at least the following: obtaining a desired breathing phase for consuming another media content comprised in a sequence comprising the first media content; determining a difference measure between the first media content and the another media content with respect to the corresponding desired breathing phases; and determining the changed breathing sequence to minimize the difference measure.

\* \* \* \* \*